US008725234B2

(12) United States Patent
Cao et al.

(10) Patent No.: US 8,725,234 B2
(45) Date of Patent: *May 13, 2014

(54) SYSTEMS, DEVICES, AND METHODS EMPLOYING FIBER OPTIC SHAPE TRACKING

(75) Inventors: Caroline G. L. Cao, Dayton, OH (US); Peter Y. Wong, Brighton, MA (US); Lothar Lilge, Toronto (CA); Paul Milgram, Toronto (CA)

(73) Assignees: Tufts University, Medford, MA (US); The Governing Council of The University of Toronto, Toronto, Ontario (CA); University Health Network, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,813

(22) Filed: Jun. 18, 2012

(65) Prior Publication Data

US 2012/0259211 A1    Oct. 11, 2012

Related U.S. Application Data

(63) Continuation of application No. 12/248,380, filed on Oct. 9, 2008, now Pat. No. 8,219,180.

(60) Provisional application No. 60/979,246, filed on Oct. 11, 2007.

(51) Int. Cl.
*A61B 5/00* (2006.01)

(52) U.S. Cl.
USPC ........... 600/424; 600/117; 600/431; 600/435; 600/478; 600/585; 385/13; 385/141

(58) Field of Classification Search
USPC ......... 600/407, 424, 431, 435, 476, 478, 479, 600/117, 585; 385/12, 13, 123, 141
See application file for complete search history.

(56) References Cited

U.S. PATENT DOCUMENTS

| | | | |
|---|---|---|---|
| 5,752,513 A | 5/1998 | Acker et al. | |
| 6,127,672 A | 10/2000 | Danisch | |
| 6,246,901 B1 | 6/2001 | Benaron | |
| 6,470,205 B2 * | 10/2002 | Bosselmann et al. | 600/424 |
| 6,514,277 B1 * | 2/2003 | Lilge et al. | 607/88 |
| 6,563,107 B2 | 5/2003 | Danisch | |
| 6,846,286 B2 * | 1/2005 | Suzuki et al. | 600/145 |
| 6,915,043 B2 * | 7/2005 | Rio et al. | 385/37 |
| 7,054,513 B2 * | 5/2006 | Herz et al. | 385/12 |
| 7,813,784 B2 * | 10/2010 | Marquart et al. | 600/424 |
| 7,930,065 B2 * | 4/2011 | Larkin et al. | 700/245 |
| 2005/0063197 A1 * | 3/2005 | Nightingale et al. | 362/551 |

(Continued)

OTHER PUBLICATIONS

Cirocco and Rusin "Fluoroscopy: A Valuable ally during difficult colonoscopy." Surgical Endoscopy, 10, 1080-1084 (1996).

(Continued)

*Primary Examiner* — Ruth S Smith
(74) *Attorney, Agent, or Firm* — Tanya A. Arenson; Casimir Jones, S.C.

(57) ABSTRACT

The present invention provides systems, devices, and methods employing fiber optic shape and position tracking. The systems, devices, and methods permit measurement of and continuous tracking of the shape and position of objects whose shape dynamically changes with time. Applications include tracking and monitoring of endoscopes for diagnostic and surgical procedures.

22 Claims, 9 Drawing Sheets

(56) References Cited

U.S. PATENT DOCUMENTS

| | | | |
|---|---|---|---|
| 2007/0106114 A1 | 5/2007 | Sugimoto et al. | |
| 2007/0116415 A1 | 5/2007 | Kobayashi | |
| 2007/0219410 A1* | 9/2007 | Onoda et al. | 600/117 |
| 2008/0188722 A1* | 8/2008 | Markle et al. | 600/316 |

OTHER PUBLICATIONS

Shah et al., "Effect of Magnetic Endoscope Imaging on Colonoscopy Performance: A Randomised Controlled Trial." The Lancet 356(18) 1718-1722 (2000).

Wehrmann & Fruhmorgen, "Evaluation of a New Three-Dimensional Magnetic Imaging System for Use During Colonoscopy." Endoscopy, 34(11), 905-908 (2002).

Cheung et al., "Improvement in Colonoscopy Performance With Adjunctive Magnetic Endoscopic Imaging: A Randomized Controlled Trial." Endoscopy 38, 214-217 (2006).

Ambardar et al., "A Preliminary Prospective Study of the Utility of a Magnetic Endoscope Locating Device During Colonoscopy." Proc. SAGES 2004 Annual Meeting (p. 74) Denver, CO, Mar. 31-Apr. 3, (2004).

Shah et al., "Effect of Magnetic Endoscope Imaging on Patient Tolerance and Sedation Requirements During Colonoscopy : A Randomized Controlled Trial." Gastrointestinal Endoscopy, 55(7), 832-837 (2002).

Carrozza et al., "A SMA-actuated Miniature Pressure Regulator for a Miniature Robot for Colonoscopy." Sensors and Actuators A, 105, 119-131 (2003).

Ng et al., "Development of a Robotic Colonoscope." Digestive Endoscope, 12, 131-135, (2000).

Tsumura et al., "Usefulness of Oblique Transparent Cylinders in Facilitating Colonoscopy." Digestive Endoscopy, 15, 121-124 (2003).

Saunders, et al., "First clinical results with a real-time electronic imager as an aid to colonoscopy." Gut, 36:913-917 (1995).

Brooker, et al., "A new variable stiffness colonoscope makes colonoscopy easier: a randomized controlled trial." Gut, 46, 801-805 (2000).

* cited by examiner

Detector 15

SYSTEMS, DEVICES, AND METHODS EMPLOYING FIBER OPTIC SHAPE TRACKING

This application is a continuation of U.S. patent application Ser. No. 12/248,380, filed Oct. 9, 2008, now U.S. Pat. No. 8,219,180, which claims priority to provisional patent application Ser. No. 60/979,246, filed Oct. 11, 2007, each of which is herein incorporated by reference in its entirety.

FIELD OF THE INVENTION

The present invention provides systems, devices, and methods employing fiber optic shape and position tracking. The systems, devices, and methods permit measurement of and continuous tracking of the shape and position of objects whose shape dynamically changes with time. Applications include tracking and monitoring of endoscopes for diagnostic and surgical procedures.

BACKGROUND OF THE INVENTION

Four million people world wide suffer from inflammatory bowel disease (IBD), in the form of Crohn's disease or ulcerative colitis. More than 600,000 people in the US suffer from some form of IBD, costing up to $1 billion in missed work per year. Moreover, IBD is associated with increased risk for colon cancer. Colorectal cancer is the second leading cause of cancer death in the US and Canada (National Cancer Institute, 2005; Canadian Cancer Society, 2006). 148,610 new cases of colon cancer in 2006 were projected in the US alone, with the cost of colorectal cancer treatment reaching $8.4 billion (in 2004 dollars) per year (NCI, 2005). In 2008, nearly 150,000 Americans will be diagnosed with colorectal cancer and 50,000 of those will die from colon cancer (American Cancer Society, 2007). The cost-effectiveness benefits for screening, compared with no screening, range from $10,000 to $25,000 per life year saved (National Committee for Quality Assurance, 2004).

Currently, colonoscopy is the most sensitive test for diagnosing IBD and screening for colon cancer. In colonoscopy, a flexible endoscope is used to examine the inner wall of the entire length of the large intestine, from the rectum to the caecum. Even though colon cancer is 90% successfully treated if detected at an early stage, the compliance rate for screening is only 30% in the United States. This resistance to regular colonoscopies is due, in large part, to the fact that the procedure is extremely uncomfortable. The uncomfortable nature of the procedure is due, in part, to the trial-and-error manipulations of the scope in order to navigate the flexible and elastic colon. In particular, loops can form in the flexible endoscope anywhere along the length of the scope. Loops can inflict a great deal of pain and discomfort on the patient. Loops can also lead to physician disorientation in the colon, resulting in misdetection of lesions and incorrect localization that can lead to unnecessary patient pain and suffering. In addition, the procedure may be abandoned before its completion due to difficulty in 'near-blind' navigation. The lack of full visual guidance in these procedures is often the bottleneck in the completion of colonoscopy procedures. Therefore, a robust tracking and guidance system that can provide position and shape information for the colonoscope is needed.

SUMMARY OF THE INVENTION

The present invention provides systems, devices, and methods employing fiber optic shape and position tracking. The systems, devices, and methods permit measurement of and continuous tracking of the shape and position of objects whose shape dynamically changes with time. Applications include tracking and monitoring of endoscopes for diagnostic and surgical procedures.

For example, in some embodiments, the present invention provides a system comprising a medical device comprising at least one (e.g., two or more) optical fiber, the optical fiber comprising a plurality of sensors configured to report the shape (e.g., bend, pitch or yaw) and position of the medical device. In some embodiments, the medical device comprises a guide wire. In some embodiments, the medical device comprises an endoscope (e.g., a colonoscope). In some embodiments, the sensors comprise a plurality of fluorophores (e.g., dyes or quantum dots) having different spectral properties. In some embodiments, the plurality of sensors are spaced along the length and circumference of the optical fiber at defined locations. In some embodiments, the different circumferential locations are approximately 120 degrees apart from one another. In some embodiments, the sensors are embedded in a region of the fiber created by removal of a portion of a buffer and/or cladding layer of the fiber. In some embodiments, the system further comprises a data collection and analysis component. In some embodiments, the data collection and analysis component comprises a detector configured to detect signal from the sensors, a computer processor for processing data associated with the signal to generate shape information, and a user interface for displaying the shape information to a user. In some embodiments, the user interface further displays an image of an environment located at the distal end of the medical device.

In further embodiments, the present invention provides a method for determining the shape of a medical device, comprising: inserting a medical device (e.g., a colonoscope) comprising an optical fiber, the optical fiber comprising a plurality of sensors into an environment (e.g., a colon); and detecting the shape of the medical device in the environment by collecting information from the sensors.

In additional embodiments, the present invention provides a method of manufacturing a medical device as described herein, comprising: modifying an optical fiber by removing a portion of a buffer and/or cladding material of the optical fiber to create a plurality of cavities and inserting sensors into the plurality of cavities; and associating the optical fiber with a medical device such that the fiber is positioned to detect the shape of the medical device.

DESCRIPTION OF THE FIGURES

FIGS. 4A and B show looping of a device of embodiments of the present invention that can occur during a colonoscopy.

DEFINITIONS

As used herein, the term "sensors" refers to any molecule or compound that generates a detectable signal. In some embodiments, sensors emit light. For example, in some embodiments, sensors are fluorescent dyes or quantum dots.

As used herein, the term "shape," for example when used in reference to an optical fiber, refers to the physical configuration of the optical fiber. Examples of shapes include, but are not limited to, the bend of the optical fiber, the pitch of the optical fiber, and the yaw of the optical fiber.

DESCRIPTION OF THE INVENTION

The present invention provides systems, devices, and methods employing fiber optic shape and position tracking. The systems, devices, and methods permit measurement of and continuous tracking of the shape and position of objects whose shape dynamically changes with time. Applications include tracking and monitoring of endoscopes for diagnostic and surgical procedures. The technology is applicable to medical devices such as endoscopes, used in a wide range of medical procedures involving, for example, monitoring or treatment of the gastrointestinal tract (e.g., esophagus, stomach, duodenum, small intestine, colon, bile duct), respiratory tract (e.g., nose, lower respiratory tract), urinary tract, female reproductive systems (cervix, uterus, Fallopian tubes), normally closed body cavities (e.g., abdominal or pelvic cavity, interior of a joint, organs of the chest), amnion, and fetuses. Procedures include, but are not limited to, esophagogastroduodenoscopy, colonoscopy, proctosigmoidoscopy, endoscopic retrograde cholangiopancreatography, duodenoscope-assisted cholangiopancreatoscopy, intra operative cholangioscopy, rhinoscopy, bronchoscopy, cystoscopy, colposcopy, hysteroscopy, Falloscopy, laparoscopy, arthroscopy, thoracoscopy, mediastinoscopy, amnioscopy, fetoscopy, and plastic surgery. The technology is also applicable to other medical devices where shape and position tracking is desired. For example, the technology may also be applied to guide wires used, for example, in cardiovascular applications. Such uses permit the practitioner to more efficiently track and image medical devices for location and shape validation, particularly reducing the number of x-ray based imaging procedures required for positioning validation, and thus reducing the time and radiation exposure required per procedure. A wide variety of non-medical uses of endoscope also exist, including, but not limited to, pre-visualization of scale models of proposed building and cities (architectural endoscopy), internal inspection of complex technical systems (borescope), examination of improvised explosive devices by bomb disposal personnel, surveillance via tight spaces, machining, computer repair, espionage, locksmithing, safe-cracking, computer forensics, and any number of other applications. Much of the description below is illustrated using a medical endoscope in the context of a colonoscopy. It should be understood that this is simply an illustration of the invention and that the concepts described herein may be applied to many other systems, devices, and methods.

Advances provided by embodiments of the present invention achieve results not available with existing technologies. At the present time, there is no easy way to measure and continuously track the shape of objects whose shape dynamically changes with time. Companies such as Measurand (New Brunswick, Canada) have developed fiber optic sensor technology using flexible arrays of distributed sensors (See e.g., U.S. Pat. Nos. 6,563,107 and 6,127,672, herein incorporated by reference in their entireties). The sensors measure shape as a data set of positions and orientations along a curve or throughout an area or volume. Corresponding hardware and software products provide the measurement and control of shapes from static poses to moving events in applications such as virtual reality and geoscience. However, this technology is not suitable for shape measurements made on devices that are cylindrical and are highly flexible, especially in terms of twist, and which have a small bend radius. For example, the Measurand SHAPETAPE does not function well when applied to a medical device such as a colonoscope. When the SHAPETAPE product is attached to a commercial colonoscope, it is difficult to affix it and the bending radii of the colonoscope is such that the internal SHAPETAPE fibers tend to break. The SHAPETAPE is also not configured for accurate measurement or monitoring of pitch and yaw, independently, at different segments along the device due to the flat 1-dimensional structure of the SHAPETAPE. It is also not suitable for tracking small devices such as guidewires which require a much smaller cross section of the shape sensitive device. Embodiments of the present invention overcome these problems.

Other limited attempts have been made, in the context of colonoscopic examinations, to improve navigation and tracking. Yet none have achieved the benefits provided by the systems, devices, and methods of the present invention. For example, Cirocco & Rusin (Fluoroscopy: A valuable ally during difficult colonoscopy. *Surgical Endoscopy,* 10, 1080-1084 (1996)) have advocated the use of fluoroscopy to guide colonoscopic examination, as well as for learning scope intubation techniques. However, most hospitals do not have such equipment readily available in their endoscopy suites. Furthermore, some endoscopists find fluoroscopy too time-consuming, as it requires the interruption of the procedure to take the x-ray pictures, which are only static 2D images. Also, the patient is unnecessarily exposed to excessive radiation with fluoroscopy.

More recent developments have steered away from the use of external radiation for tracking. Shah and colleagues have shown that by using magnetic endoscope imaging (Olympus UPD ScopeGuide), a non-radiographic technique for imaging the colonoscope shaft in real-time, performance of colonoscopy can be improved (Saunders et al., First clinical results with a real-time electronic imager as an aid to colonoscopy. *Gut,* 36:913-917 (1995); Shah et al., Effect of magnetic endoscope imaging on colonoscopy performance: a randomised controlled trial. *The Lancet,* 356(18), 1718-1722 (2000)). Other studies have shown no benefit with the Olympus system in terms of performance measures, except for the precise location of loops (Wehrmann & Fruhmorgen, Evaluation of a new three-dimensional magnetic imaging system for use during colonoscopy. *Endoscopy,* 34(11), 905-908 (2002)), and the endoscopists' self-reported ease of locating lesions (Cheung et al., Improvement in colonoscopy performance with adjunctive magnetic endoscopic imaging: A randomized controlled trial. *Endoscopy,* 38, 214-217 (2006)). Currently marketed by Olympus, this system uses three large electromagnet generator coils placed adjacent to the patient, to generate sequential pulses of low strength electro-magnetic fields. A series of 12-15 sensor coils spaced at 12 cm intervals is built into the endoscope. Every 0.2 seconds, the tiny voltage induced in each of the sensor coils, responding to the magnetic pulses from the generator coils, is computed to give the position and orientation of each sensor. The position and orientation information is presented on a computer generated 2D display, with anatomical markers to indicate the positions of various organs surrounding the colon, as well as grey shadings to create a 3D effect. Clinical results showed that time to task completion was faster and the number of attempts at straightening loops in the scope was reduced (Shah et al, 2000). However, patient tolerance of pain and sedation requirements were not improved (Ambardar et al., A preliminary prospective study of the utility of a magnetic endoscope locating device during colonoscopy. Proc. SAGES 2004 Annual Meeting, (pg. 74) Denver, Colo., Mar. 31-Apr. 3, 2004; Shah et al., Effect of magnetic endoscope imaging on patient tolerance and sedation requirements during colonoscopy: a randomized controlled trial. *Gastrointestinal Endoscopy*, 55(7), 832-837 (2002)). A technical limitation of this method is that it requires the placement of large magnetic coils near the operating table, which may be subject to interference when other metal objects such as surgical instruments are in the vicinity. In addition, the costs associated with buying the new system (new scope, new tower with electromagnetic receiver, and monitor), disposal of the current colonoscopes, as well as the physical space needed to accommodate the system, are deterrents to its adoption in North American hospitals and clinics.

Other researchers have experimented with mechanical solutions, such as a robotic colonoscope (Carrozza et al., A SMA-actuated miniature pressure regulator for a miniature robot for colonoscopy. *Sensors and Actuators A*, 105, 119-131 (2003); Ng et al., Development of a robotic colonoscope. *Digestive Endoscopy*, 12, 131-135 (2000)), oblique transparent cylinders (Tsumura et al., Usefulness of oblique transparent cylinders in facilitating colonoscopy. *Digestive Endoscopy*, 15, 121-124 (2003)), and using a body with graduated stiffness to gain more control over the behavior of the scope (Brooker et al., A new variable stiffness colonoscope makes colonoscopy easier: a randomized controlled trial. *Gut*, 46, 801-805 (2000)). For example, graduated stiffness colonoscopes by Pentax and Olympus are designed to be more stiff as they are inserted into the colon, or have an adjustable stiffness feature. The latter has been shown to be effective at eliminating looping approximately 65% of the time, with less pain inflicted on the patients (Brooker et al., 2000). Nevertheless, these techniques remain largely dependent on experience and trial-and-error manipulations, and limited by the lack of visual guidance.

Others have endeavored to circumvent the need to perform colonoscopies, by doing virtual colonoscopies, or by using wireless ingestible capsules for small bowel inspection only. Virtual colonoscopy is a new method of imaging the colon in which thin-section, helical computed tomography (CT) is used to generate high-resolution, two-dimensional axial images. Three-dimensional images are then constructed off-line. These devices are currently being developed by Viatronix, Inc. Since virtual colonoscopy is a non-invasive procedure, it can be used only for diagnosing cancerous lesions and polyps. As a result, it will not replace current colonoscopes as a therapeutic device. However, it is a fast, cost-effective and comfortable procedure and does hold promise for future use as a mass screening tool. Endoscopists believe that it will take many more years of development before the difficulties associated with virtual colonoscopy will be overcome. Such difficulties include: diagnostic accuracy, the need for bowel cleansing and infusion of gas to expand the colon, and the need to train highly skilled technicians in the interpretation of images. Ingestible capsule is another non-invasive alternative. These capsules can take images of the stomach and small bowel as it passes through them unaided. An antenna array is attached to the patient, where a wireless recorder, worn on a belt around the patient's waist, records the signals transmitted by the capsule to the array. The image sensor is designed by Photobit Corporation and the disposable capsule-camera is marketed by Israel-based Given Imaging Ltd. This device can be used for diagnosing small intestine disorders. None of these proposed solutions address the problem of orientation in the navigation process, with or without loop formation.

I. Devices

Figure 5:
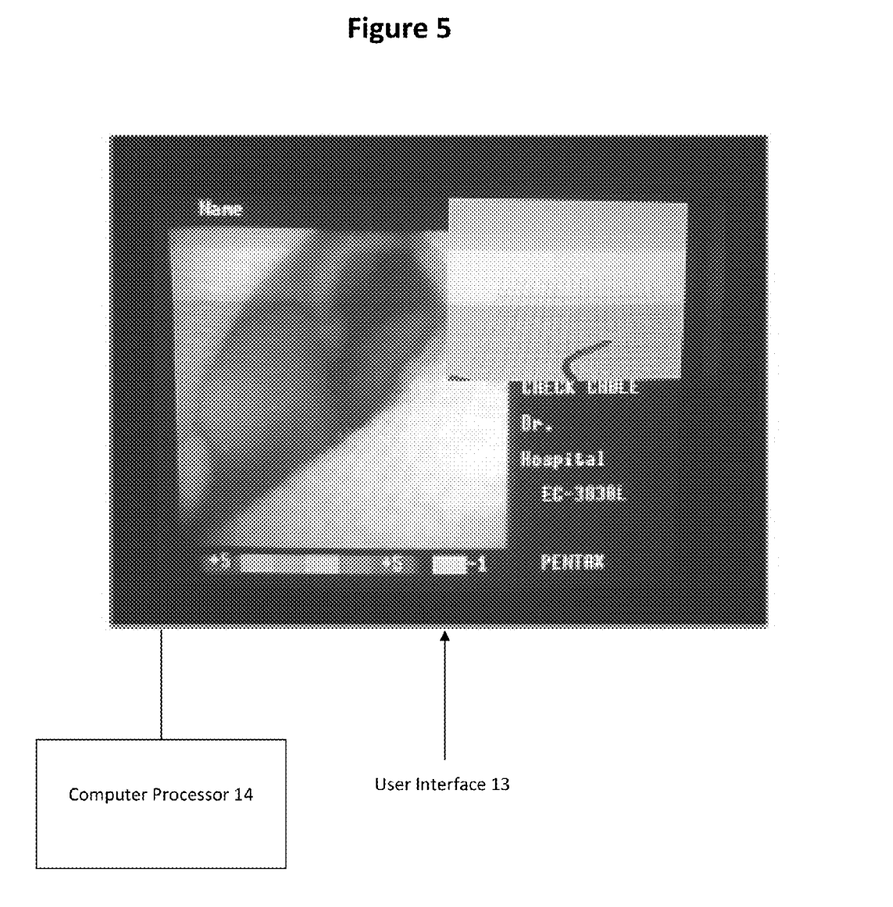
FIG. 5 shows an exemplary colonoscopy setup using the shape tracking device showing a user interface 13 and a computer processor 14 of embodiments of the present invention.
Figure 7:
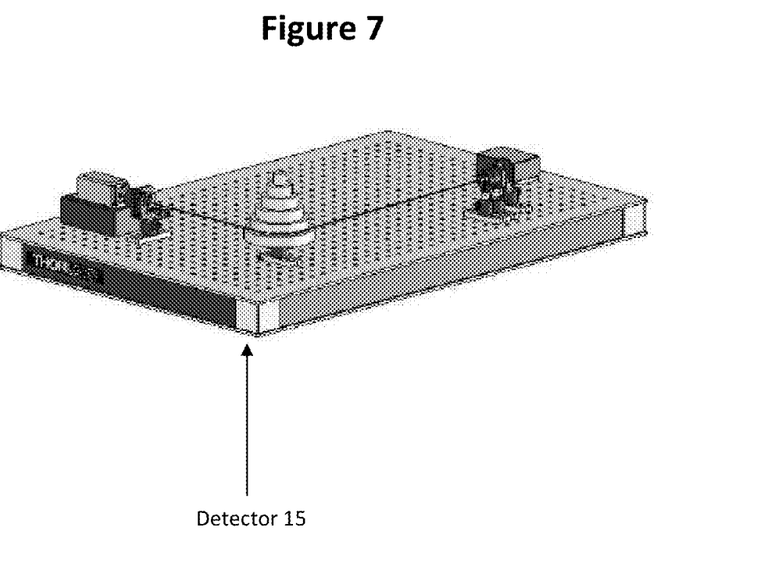
FIG. 7 shows a detector apparatus 15 for detecting signal from exemplary devices of the present invention.

Exemplary devices of the present invention are described below. One skilled in the art recognizes that modifications and substitutions of the below described devices are within the scope of the present invention. FIG. 5 shows an exemplary colonoscopy setup using the shape tracking device showing a user interface 13 and a computer processor 14 of embodiments of the present invention. FIG. 7 shows a detector apparatus (e.g., spectrometer) 15 for detecting signal from exemplary devices of the present invention.

A. The Colonoscope

Figure 4:
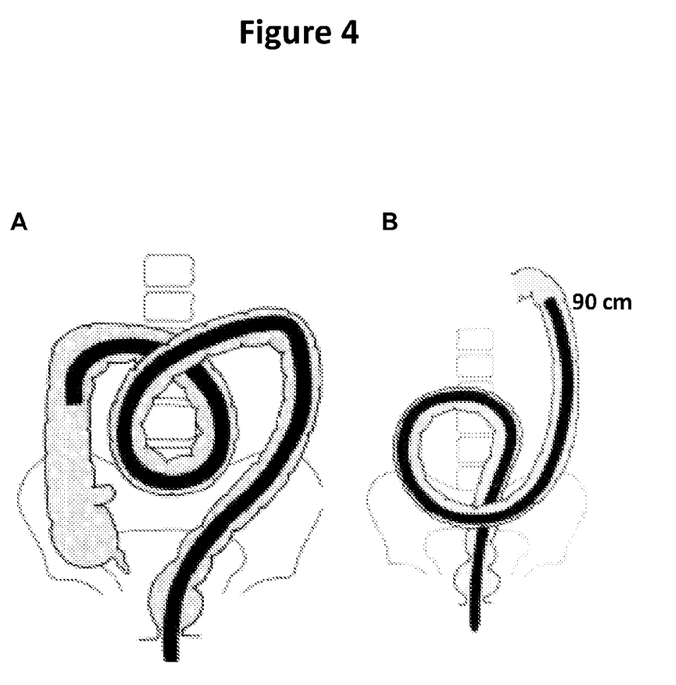
Figure 6:
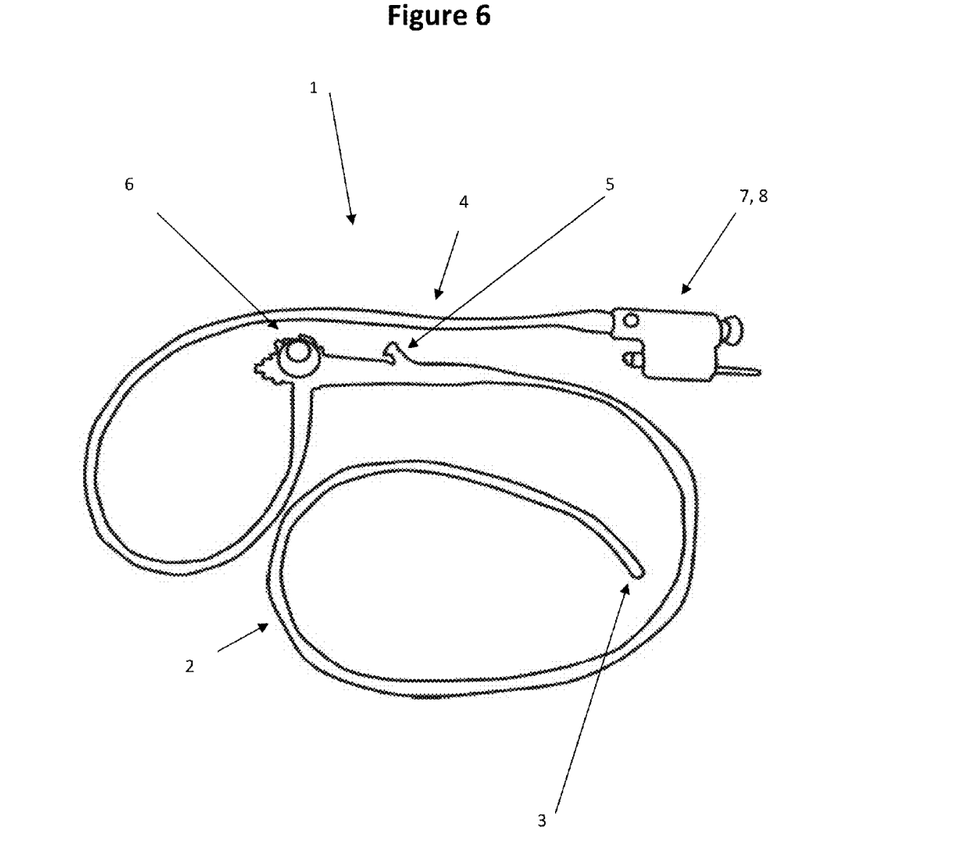
FIG. 6 shows an exemplary flexible endoscopy for colonoscopy.

The colonoscope is a specialized flexible endoscope used to inspect the colon of the patient (see FIGS. 4-6). An exemplary colonoscope (1) is illustrated in FIG. 6. The colonoscope (1) is comprised of several main parts, the shaft (2), articulating end (3) (~6 cm at the end), body (4), biopsy channel (5), handle (6), optical bundle (7) and video connection/optical eyepiece (8). The shaft of the colonoscope is typically 140-180 cm long and is flexible, allowing for bending inside the body. However the shaft is stiff when pushed in the axial direction, allowing for advancement of the scope inside the body. The distal tip of the endoscope generally has an internal vertebra capable of 2-way articulation (pitch and yaw). The articulation is controlled by two turn wheels located on the handle; one wheel controls the pitch while the other controls the yaw. FIGS. 4A and B show looping of a device of embodiments of the present invention that can occur during a colonoscopy. FIG. 5 shows an image of the view through a colonoscope using an exemplary colonoscopy setup using the shape tracking device of embodiments of the present invention.

Inside the shaft contains the light guide, image bundle and the working channel. The light guide is a bundle of optical fibers used to transmit light from an external light source to the viewing area within the body. The light guide enables a high power external light source to be used without having to deal with the size and heat requirements of having the source inside the body. The image bundle also uses optical fibers like the light guide. However, in the image bundle the fibers should be aligned so that an image that passes into the fiber bundle will exit the fiber in the same orientation. Depending on the model of colonoscope, the image bundle will either terminate at an eyepiece, or connect to an image processor to be processed digitally and displayed on a monitor.

B. Optical Fibers

Optical fibers use the property of total internal reflection to "trap" and allow light to propagate through it without escaping to the surroundings. The fiber is constructed using materials with different refractive indexes. The "core" or the inner medium upon which the light is transmitted has a high refractive index, while the "cladding" that surrounds the core has a lower refractive index. The difference in refractive index between the core and cladding is normally around 1% or less. Assuming that the difference in refractive indices is 1%, the confinement angle, the largest allowable angle that will confine the light in the core, is around 8°. In cases when light propagating in the fiber strikes the cladding at a greater angle than the confinement angle, total internal reflection will not take place and a portion of the light will escape the fiber. This occurs when the fiber is bent, resulting in an increased internal reflection angle of the light beyond the confinement angle. This allows the light to escape the core and is known as bendloss.

Optical fiber has many uses, such as light guides and image bundles in endoscopes, and as mechanical strain gauges and chemical sensors. However, the biggest driving force behind optical fibers is the telecommunication industry. Since the invention of the first laser in 1960 by Theodore Mainan, new optical fibers and methods are being developed to transmit signals farther and with higher bandwidth.

Two main categories of fibers exist, single-mode and multimode. Modes are stable patterns that light forms when traveling through a fiber. Single-mode fibers transmit only one mode of light, allowing for high signal quality, but since the core of the fibers is relatively small it becomes tedious to input the light. Multi-mode fibers have larger core diameters so coupling is not as difficult, but the signal quality is weaker due to the fiber's susceptibility to loss of the higher modes through bendloss.

In some embodiments, the tracking components of the present invention employ a fiber optic device. In some embodiments, the component is based upon a single fiber operation. For example, a single fiber of arbitrary length is combined with multiple sensing elements along its length. By removing portions of the buffer around the fiber and/or the cladding, and depositing a detectable material in the portion removed, light passing down the fiber is differentially reflected at that point, depending on the degree of bending. For example, narrow bandwidth (e.g., produced from a laser or filtered white light source) is introduced at the proximal end of the fiber. If the fiber is not completely straight, some of the light leaks out of the core, through the cladding, and is commonly absorbed by the buffer. The amount of leakage at the outer arch of a bend depends on the radius of bending. To convert leakage into a positive measurable quantity, the fiber contains at predetermined positions, materials that are comprised of fluorophores or other luminescent materials. The fluorophore may be contained in epoxy or other suitable material and placed into a previously removed portion of the fiber buffer and/or cladding. Filtering materials (e.g., light absorbing dyes, thin films, or spatially patterned structures) may be contained in the removed portion of the fiber to sharpen the spectral emission response. One or more light sources may be used to introduce light into the fiber. Likewise, one or more detectors may be used to measure signal from the fluorophores or other signal-generating materials used.

In some embodiments, the entire sensor is implemented with a single fiber. However, two or more fibers may be used. In the case of colonoscopes, for example, it is possible to insert a single fiber into one of the channels of the instrument. For example, it can be inserted into the biopsy channel of the colonoscope, or embedded in the body of the colonoscope to track the position and shape of the scope in real-time. The position data may be used to drive a 3D graphical model of the scope in real-time, which then serves as a navigational aid for the physician during the colonoscopy procedure. Because the device is relatively inexpensive, disposable devices are contemplated.

Thus, in some embodiments, the present invention provides an endoscope comprising one or more fibers having a plurality of sensors positioned along their length to permit shape and/or position tracking. The devices may be combined with other medical devices and systems, including imaging hardware and software. In some embodiments, the sensor provides two- or three-dimensional data for the purpose of spatial visualization by practitioners, in real-time. By tracking shape and position, coupled with effective display design, visualization and navigation of the endoscope or other device becomes much more effective. For example, in some embodiments, a display of the shape and location of the endoscope is provided along with (e.g., on the same monitor) images acquired at the tip of the endoscope. Among other benefits, the implementation of such a system permits improved detection, diagnosis, and therapy.

The systems, devices, and methods of the invention provide benefits for a number of different entities. For the physician, such a shape sensor device can be coupled with a visual guidance system to reduce disorientation during colonoscopy, lower mental and physical workload in manipulating the scope, better decision-making, and more accurate diagnosis. For the patient, this means that the procedure might be shorter, with fewer colon-stretching maneuvers, and less pain and discomfort. For the hospital, it may mean smaller or fewer dosages of anesthesia, and more patients examined per day. For the health care system, it may mean lower healthcare costs due to earlier detection of IBD and cancer.

C. Fluorophores

Fluorophores are unique compounds that emit light when excited by light. When their electrons that are excited to upper energy levels decay down, the energy change is radiative and a photon is released; this is known as fluorescence. It is this unique property that leads to their heavy use in biological imagery. There are two main types of fluorophores, endogenous and exogenous fluorophores. Endogenous fluorophores are found naturally within the body and emit an autofluorescence that is very helpful for spectroscopy. Exogenous fluorophores are molecules that are not found naturally in the body. These fluorescent dyes (exogenous fluorophores) when excited will emit a distinct longer wavelength light than the excitation light wavelength due to Stokes shift. The shift to a longer wavelength in fluorescence is caused by energy that is lost to non-radiative forms during electron decay. These exogenous fluorophores are also very important to spectroscopy and other applications. In particular, they can be used as fluorescent dyes for things that don't naturally fluoresce.

There are many organic dyes (exogenous) to choose from when selecting dyes for a specific application. Organic dyes, however, can only be excited with certain wavelengths so it is preferred to choose a dye that will work with a specific light source. The choice of excitation and emission wavelengths is considered when using more than one dye in a single sample. The excitation wavelengths of the two dyes is preferably the same or very similar so that both dyes can be used with the same light source. Emission wavelengths of the two dyes are also preferably far enough apart that the two distinct dyes can be distinguished.

The present invention is not limited by the nature of the sensors used to track position and shape. Any sensor that permits detection of light associated with bends in the devices may be used. In some embodiments, the sensor is a fluorophore. Fluorescent dyes include, but are not limited to, 7-amino-actinomycin D, acridine orange, acridine yellow, auramine O, auramine-rhodamine strain, benzanthrone, 9,10-Bis(phenylethynyl) anthracene, 5,12-Bis(phenylethynyl) naphthacene, CFDA-SE, Calcein, Carboxyfluorescein, 1-Chloro-9,10-bis(phenylethynyl)anthracene, 2-Chloro-9,10-bis(phenylethynyl)anthracene, Coumarin, Cyanine, DAPI, Dark quencher, Dioc6, DyLight Fluor, Ethidium bromide, Fluorescein, Fura-2, Fura-2-acetoxymethyl ester, Green fluorescent protein, Hilyte Fluor, Hoechst stain, Indian yellow, Luciferin, Perylene, Phycobilin, Phycoerythrin, Phycoerythrobilin, Rhodamine, RiboGreen, Rubrene, Ruthenium(II) tris(bathophenanthroline disulfonate), SYBR Green, Stilbene, TSQ, Texas Red, Umbelliferone, and Yellow fluorescent protein.

In some embodiments, release of quenching is used to generate light. For example, in some embodiment a dye and a quencher are located in proximity to one another and a bend or other shape change shifts the location to remove or reduce the quenching, causing an increase in detectable signal.

In some embodiments, the sensor is a quantum dot. Quantum dots are nanostructure semiconductor fluorophores with diameters on the order of 2-10 nm. Unlike traditional organic dyes, quantum dots' fluorescence is not reliant on their chemical structure. Quantum dots composed of the same compound can emit fluorescence at different wavelengths by variations in their size. This quantum confinement effect is caused when the dimensions of a quantum dot are smaller than Bohr's radius. When this happens the band gap or distance between energy levels is proportional to the size of quantum dot. As the size of the particle decreases, the distance between the energy levels increases creating the need for more energy (lower wavelength light) to cause an electron to be excite to the next level. Since smaller quantum dots require more energy to excite, they also emit more energy which results in a shorter wavelength emission than larger quantum dots.

The characteristics of the quantum dots to emit different wavelengths as a function of particle size create many advantages over traditional organic dyes. One such advantage is that quantum dots can be excited with any wavelength light that has enough energy to cause an electron to cross the band gap. As long as the light source is chosen for the smallest quantum dot (requires the most excitation energy) all other quantum dots of larger size can be excited as well (see FIG. 9). This eliminates the painstaking process of finding organic dyes that can be excited using a single coherent source.

Quantum dots also differ from organic dyes in that they are not as susceptible to the photobleaching effect. When compared with Rhodamine 6G, quantum dots were nearly 100 times more stable (Chan et al., Science 281, 2016-2018 (1998)). This enables quantum dots to be implemented in longer-term situations where organic dyes currently are not able to perform. Another advantage of quantum dots is that they have a slim, symmetric emission bandwidth compared to the wide, asymmetric emission bandwidth of organic dyes (Bailey et al., Physica E: Low-Dimensional Systems and Nanostructures 25, 1-12 (2004). This allows for many dyes to be used in the same sample with minimal overlap in emission spectra. This is useful in systems that utilize modified buffer locations on a single fiber in a multi-axis shape-tracker.

By spacing similarly treated locations at 120 degree intervals around the fiber at that segment, and computing differential signal strengths, it is possible to sense two degrees of freedom of bending of that segment—i.e., pitch and yaw. In other words, for example, if the sensing areas are spaced as dual pairs at 90 degree intervals, when the fiber bends in one direction, light will leak from the portion along the outer radius of the bending curve. If bending is in the opposite direction, the opposite spot will fall along the outer curve. If bending is orthogonal to this, the other two locations will be activated. Taking all signals together provides the bending signal in any direction for that segment. The position of the locations need not be at 120 degree intervals. Any combination of intervals may be used, so long as the signal collected can be measured and deconvoluted to provide the desired information.

Within each segment, different wavelengths of light are combined, corresponding to the number of sensor sections used around the circumference (e.g., minimum 3) and the number of fluorophore wavelengths used, in order to identify from which of the locations the light is leaking due to bending. A spectrometer may be used at the exit of the fiber to identify the different bending signals. The spectrometer signal may be calibrated to relate the degree of bending to the spectrometer output for each wavelength of light.

Along the length of each single fiber, a number of these sensing "clusters" may be placed, so that an approximation can be made to the shape of the entire fiber. Different dyes may be used in a multiplex fashion, so that it is possible to know which segment of the fiber is being signalled at any one time. Appropriate software is used to enable integration of the signals from all of the sensing clusters, in order to compute the overall shape of the entire fiber.

D. Exemplary Design

Figure 1:
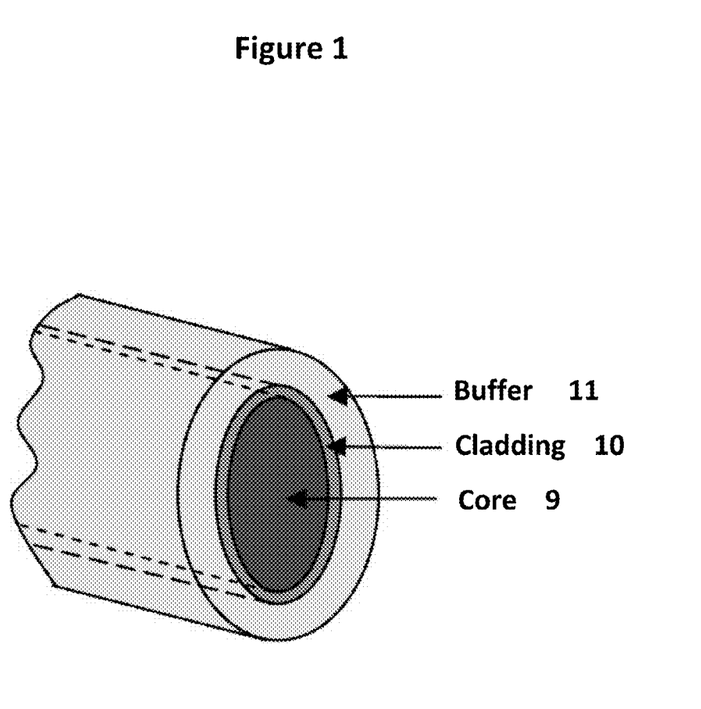
FIG. 1 shows a typical optical fiber structure.

The following description provides an illustrative example of an embodiment of the present invention. The present invention is not limited to the specific details of this embodiment. FIG. 1 shows a typical optical fiber structure.

Optical fibers measure bend by virtue of their physical structure. A typical optical fiber consists of three layers of material having different optical and structural properties. FIG. 1 illustrates the structure of an optical fiber. The 'core' (9) typically consists of an optically dense medium with a high index of refraction, $n_{core}$, and is coated with a layer of less optically dense material called the 'cladding' (10) ($n_{clad}<n_{core}$). The outermost layer, the 'buffer' (11), serves to maintain the mechanical strength of the fiber. Light propagating along the length of the fiber is contained within the core due to 'total internal reflection', as there exists a critical angle of incidence ($\theta_{crit}$) at the core/cladding interface.

Light incident on the core/cladding interface at an angle less than the critical angle will be allowed to pass through the interface. The critical angle is defined by the relationship:

$$n_{clad}=n_{core}\sin\theta_{crit}$$

Figure 2:
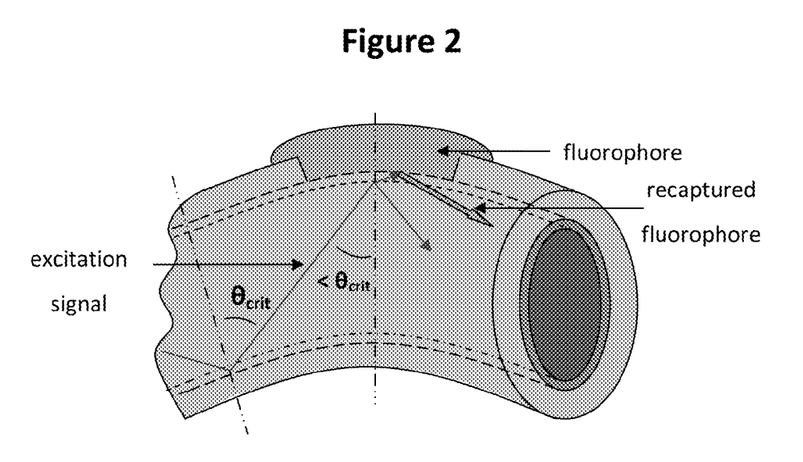
FIG. 2 shows a diagram describing fluorescence capture in a bending fiber.

An endoscopic fiber optic shape tracker (EFOST) embodiment of the present invention may be constructed from a single optical fiber with fluorophore markers embedded in the buffer and/or cladding at various positions along its length. Here, a fluorophore refers to a chemical (organic dye) or physical (quantum dot or nanocrystal) entity that when excited by light of one wavelength emits light at a different, longer wavelength band. These fluorescence emission techniques are used to detect the radius and direction of bend along the length of the optical fiber. As the fiber is bent, a portion (high numerical modes) of the excitation light is lost through the cladding, exciting the fluorophore at that location, while the low numerical modes are redistributed into the higher modes. The fluorescence emission waveband is captured at either end of the fiber, to calculate the degree of bend based on the intensity. The intensity of the emission is proportional to the amount of bend in the fiber at the point where the fluorophore has been applied to the fiber structure, as illustrated in FIG. 2.

In order to sense multiple bends in the same body using a single fiber, the reflected light from the various bends in the fiber should be differentiable. Hence, each point along the fiber is uniquely defined by a color-coded emission spectrum. Each fluorophore is characterized by its Stokes shift, or the difference between the wavelength of the excitation and emission maximum, as well as the spectral shape of the emitted light. Remittance of the fluorescent emissions via the same fiber can then be spectrally resolved and quantified. As the fluorophores are not exposed to the biomolecules of the body, their fluorescent quantum yield is constant and hence the emission intensity depends only on the excitation intensity (controlled) and the radius of the bend.

Figure 3:
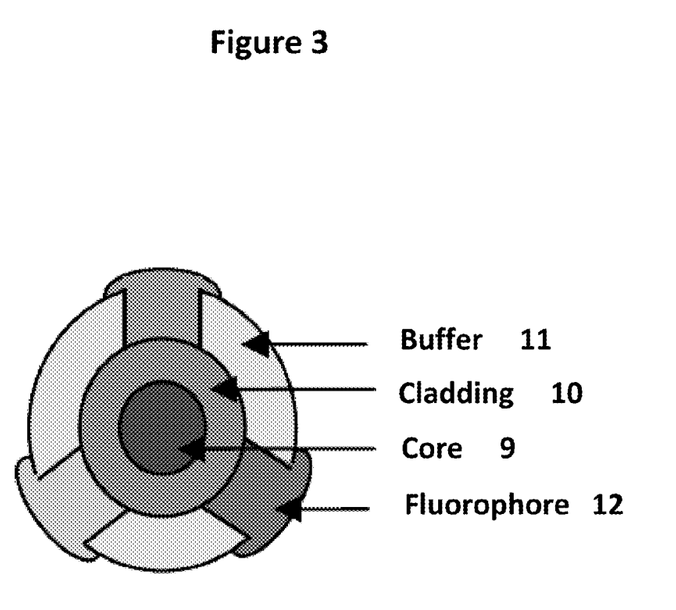
FIG. 3 shows an end on view of an exemplary device of embodiments of the present invention.

This technique can be extended to allow for measurement of any bend in 3 dimensions by placing three fluorophores with different emission spectra, spaced by, for example, 120° around the circumference of the fiber (as shown in FIG. 3), to determine which side of the fiber is on the outside of the bend. This can be achieved by measuring the relationship between the different fluorophore emissions transmitted down the fiber. In addition, by spacing rings of 3 unique fluorophores at known intervals along the length of the fiber, one can measure the location of the different segments and, hence, can determine corresponding directions of curvature at known distances along the fiber in 3D. The number of segments included in a single fiber depends on the number of distinct fluorophore emissions attainable.

In some embodiments, a fiber has sensor regions at most 6 cm apart, with a total length of at least 100 cm in order to track the majority of the length of the endoscope. With its small size, the device can easily be inserted into the biopsy channel of the scope, or mechanically integrated into the shaft of the scope, to increase its accuracy. This would also eliminate the problem of torsion, as the fiber would be housed in the biopsy channel, with one end anchored in a fixed location, such as on the operating table. This fixed point would also serve as a reference point for calculating the position and bends of the fiber for rendering purposes. When used via the biopsy channel in a single channel scope, it is possible to remove the fiber when a biopsy needle is introduced, and re-inserted when the biopsy needle is removed. Alternatively, in the case of a scope with dual biopsy channels, one channel can be dedicated to the fiber, eliminating the need to remove the sensor during the procedure.

The modified fiber may be constructed using any number of desired techniques. A standard optical fiber may be used as a starting point, with modifications made to add the sensing components. These modifications include the removal of selective regions of the fiber's protective buffer and/or cladding and the application of fluorophores to those regions. Design criteria preferably include: 1) removing the buffer and/or cladding, without significantly compromising the minimum bending radius, 2) spacing of the buffer and/or cladding holes to provide good sensitivity to the bend without limiting spatial resolution, 3) the preparation and application of the fluorophore mixture, and 4) reinforcing the final structure to restore the minimum bending radius. Methods for the removal of the buffer and/or cladding from the fiber optic include, but are not limited to, stripping using hydrofluoric acid, chemical etching, laser and mechanical micro-machining. For example, using a micro-lathe, 200 micron discs can be cut out of the buffer of the optical fiber without affecting the cladding.

A variety of methods of making a fluorophore mixture to be placed on the cladding of the fiber may be used. In some embodiments, the fluorophore solution (in methanol) is embedded in epoxy resin. The epoxy is deposited onto the optical fiber manually.

In order to be able to determine the shape of the sensor structure, the optical signals transmitted through the fiber should be analyzed and interpreted. Several fluorophores (NILB640, RHOD590, OXAZ750, AD680BP, AD680HO, AD740PP, AD745HO, AD745HT, LDS821, LD700, LDS750, CRES670, OXAZ720, AD640MT) have been tested to identify ones which emit at the highest intensities when excited with red light. Fluorophores having the largest efficiency and variant Stokes shift are selected for the sensor design so that the signals are easily identified and separated.

The emission intensity or signal gain, $\alpha_B$, is characteristic of the fiber's bend at the point where the fluorophore has been applied to the fiber structure. Considering the excitation light loss, $\alpha_1$, and fluorescence recapture, $\alpha_c$; yields $$\alpha_B = \alpha_1 * \alpha_c, \text{ where } \alpha_1 = I \exp(-R/R_c)$$

R is the bend radius and $R_c$ is a constant which depends on fiber parameters such as core diameter and numerical aperture. I is related to the excitation intensity and the surface coverage of the cladding. The time reverse effect will model the fluorescence recapture by the optical fiber core, following the same principle equation where C presents the solid angle of fluorescence recapture (for a fuller discussion on the effect of bend radius on fluorescence signal gain, see Boechat et al. Bend loss in large core multimode optical fiber beam delivery systems. *Appl Optics*, 30(3): 321-327 (1991)):

$$\alpha_c = C \exp(-R/R_c).$$

In some embodiments, the fibers are glass/glass or silica/silica based with a large numerical aperture in order to support a large number of modes for a given fiber diameter, thus maximizing the dynamic range and angular resolution of the sensor. The cladding should be sufficiently thick to prevent excitation of the fluorophore beyond the cladding by the evanescent waves of the excitation light traveling in the core. In some embodiments, fibers of 250 μm core diameter with at least a 25 μm cladding thickness and either a polyimide buffer or an acrylate buffer are used. The thinner polyimide buffer (10 μm) is preferred as it results in a thinner overall fiber sensor.

In some embodiments, 75 fluorophores are used to track 1.5 meters of the endoscope. Three distinct fluorophores form a ring around the circumference of the scope at 6-cm intervals. This provides maximum information and redundancy for local curvature determination. Spacing may be more or less than 6 cm (e.g., 3, 4, 5, 6, 7, 8, 9, 10, 11, 12, 13, 14, 15 cm apart, combinations thereof, or intervals therebetween). In some embodiments, more information is provided near the tip and the distal end of the colonoscope with more sensors, while the proximal end of the scope is more sparsely sensorized. Using time-delayed graphical rendering, historical data from the shaft of the scope could be displayed to augment the real-time graphics provided by the more densely sensorized tip of the scope. For example, in a 1-meter section of fiber, one could have 5 fluorophore rings spaced 6 cm apart near the distal tip of the scope, while the remaining 5 rings could be space 12 cm apart. Mechanical and opto-electronic switching may be used along with graphical rendering to create a full picture of the scope in real time.

In some embodiments, data analysis includes determination of the yaw and pitch of the device. Using this method, the pitch and yaw of each segment are encoded into the spectral domain. All wavelengths captured simultaneously are spectrally resolved, resulting in a set of complex emission spectra as a function of pitch and yaw. These emission spectra are then decomposed into their component fluorophores, by analytical or numerical methods, such as partial least square (PLS) or principal component regression (PCR).

EXPERIMENTAL

The following examples are provided in order to demonstrate and further illustrate certain preferred embodiments and aspects of the present invention and are not to be construed as limiting the scope thereof.

Example 1

Advanced Shape Tracking to Improve Flexible Endoscopic Diagnostics

This Example describes the development of a fiber-based shape tracker. Utilizing fiber optics and fluorophores, a shape-tracking sensor embodied in a single optical fiber was developed. The small size of a single optical fiber allows for easy integration with current endoscopes, such as by inserting through the biopsy channel. This dynamic upgrade provides an invaluable aid to clinicians, reducing disorientation and looping and ultimately making colonoscopy procedures more comfortable, shorter, and safer for patients.

A. Methods

To solve the navigational problems in colonoscopies a shape tracker with a real time display was created. The shape tracking technology utilizes a modified single optical fiber to supply all the relevant shape information about the current endoscope's shape. The optical fiber was modified by embedding fluorophores in the buffer at discrete locations. Laser light was then directed through the fiber so that when the fiber was bent, light lost through bendloss excited the fluorophores. The fluorophores emitted light at a longer wavelength back into the core. By measuring the fluorescence at the end of the fiber, fluorescence intensity was related to changes in fiber curvature.

Fiber Modification

Removing a Circular Portion of the Buffer

A 30W $CO_2$ cutting laser was used to create a circular 150 μm hole in the buffer of the fiber. To do this, a 150 μm pinhole was used as a mask because the lasing beam diameter was greater than the 150 μm hole. The first step in fiber preparation was to fix the fiber in a base plate with a channel to hold the fiber. Also in the base plate a circular hole was cut to hold the mounted pinhole above the fiber. This ensured that the 150 μm pinhole was centered over the optical fiber. Next the cutting laser was passed over the pinhole; only the portion of the beam that could pass through the pinhole penetrated allowing for a 150 μm hole to be created. Due to the different melting points for the buffer and cladding a hole was created in the buffer, leaving the cladding unscathed.

Embedding the Fluorophore

The 150 μm hole in the buffer was filled with a mixture of a fluorescent dye and ultraviolet (UV) curing epoxy resin. The organic dyes used were LD 700 Perchlorate and Oxazine 750 Perchlorate from Exciton, Inc. A 0.01M solution of dye in methanol was mixed with varying ratios of UV glue. Ratios of 1:1, 1:2, and 1:3 parts dye solution to UV glue were created and inserted into the buffer. A UV light gun was used to cure the glue, sealing the hole in the buffer.

Preparation for Testing

The modified fiber was connected to a standard SMA connection. To do this a universal bare fiber terminal (BFTU) was used so that different fiber samples could be tested using the same connectors. For the fiber to work with the BFTU one inch of the buffer was stripped off so it could be inserted into the BFTU. After insertion in the BFTU the fiber end was wet sanded using figure-eight motions through 5 μm, 3 μm and 1 μm sandpaper to polish and ensure maximum light transition for testing.

Experimental Apparatus

The experimental setup used to test the fiber was composed of a helium-neon (HeNe; 632.8 nm) laser, two collimators, a bandpass filter, a long pass filter, stepped cylinder with known radii and a spectrometer. The HeNe laser beam was passed though a 632.8 nm bandpass filter to ensure that only light with the wavelength directly surrounding the 632.8 nm would enter the fiber. After the bandpass filter the laser beam was focused using a collimator and directed into the optical fiber. At the other end of the fiber the laser light was re-collimated and passed through a long pass filter to eliminate the laser wavelength. This allowed the fluorescing wavelengths to pass and be measured using a spectrometer (see FIG. 7).

Test Procedure

The modified fibers were tested using a stacked series of cylinders with known bending radii. Once the fiber was connected to the apparatus (see FIG. 7), it was placed around the smallest ring on the stepped cylinder with the modified buffer zone positioned on the outmost radius centered in the bending zone. The spectrometer integration time setting was then adjusted so that the fluorescence intensity was utilizing the full scale of the spectrometer. A measurement of the fluorescent intensity (counts) was recorded for that bend radius. The fiber was then moved to the next larger radius and a new fluorescent intensity reading was recorded. This procedure was continued through the different size bend radii and results plotted to correlate intensity of the fluorescence to fiber bending curvature.

B. Results

Figure 8:
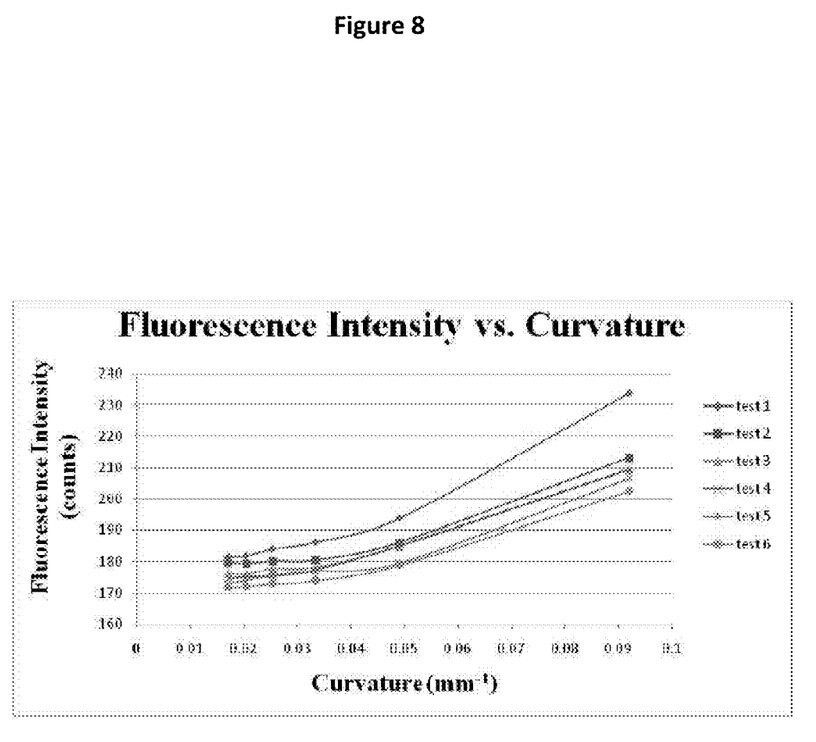
FIG. 8 shows a graph of fluorescent intensity vs. curvature.

Results showed that the process was very susceptible to changes in preparation as well as alignment settings of the experimental setup. Using LD700 organic dye in a 0.01M dye/methanol solution with a 1:1 mixture in UV glue, it was possible to obtain an excellent fluorescent intensity to curvature relationship (see FIG. 8). Also, a 40% increase in fluorescence intensity when the fibers bend was achieved as the radius decreased from 58 mm to 11 mm.

Figure 9:
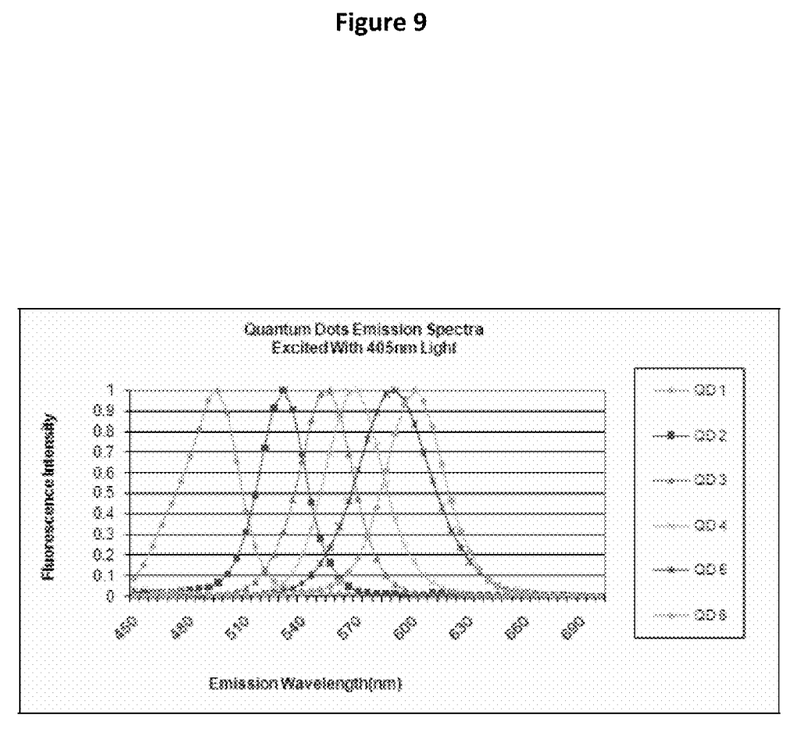
FIG. 9 shows emission spectra of quantum dots excited with 405 nm light.

In the experiments, several limitations in materials were identified. For example, the organic dyes experienced photobleaching, which can be seen in FIG. 8 as the downward vertical shift in intensity from test one to test six of the same sample. Quantum dots were investigated as an alternative since they have many properties that are beneficial over organic dyes. FIG. 9 demonstrates that as long as the light source is chosen for the smallest quantum dot (requires the most excitation energy) all other quantum dots of larger size can be excited as well.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A system comprising a) a device comprising an optical fiber, said optical fiber comprising a core and a cladding surrounding the core, wherein said cladding comprises a plurality of cavities such that light leakage from the core through said cavities in the cladding occurs when a bend is present in the fiber; and wherein said cavities contain a fluorphore that generates a fluorescent emission in response to said light leakage, and wherein the intensity of said fluorescent emission is proportional to the degree of bend in said fiber; b) a detector that measures said fluorescent emission; and c) a computer processor that processes fluorescent emission data associated with said fluorescent emission and tracks said device based on said fluorescent emission data.

2. The system of claim 1, wherein the device comprises a guide wire.

3. The system of claim 1, wherein the device comprises an endoscope.

4. The system of claim 1, wherein said device comprises two or more of said optical fiber.

5. The system of claim 1, wherein said device has a single of said optical fiber.

6. The system of claim 1, wherein said fluorophore comprises one or more organic dyes.

7. The system of claim 1, wherein said fluorophore comprises one or more quantum dots.

8. The system of claim 1, wherein said plurality of cavities are spaced along the length and circumference of the optical fiber at defined locations.

9. The system of claim 8, wherein said circumferential locations are approximately 120 degrees apart from one another.

10. The system of claim 8, wherein said detector measures said fluorescent emission at an end of said optical fiber.

11. The system of claim 1, further comprising a user interface for displaying information to a user.

12. The system of claim 11, wherein said user interface displays an image of an environment of the device.

13. The system of claim 1, wherein said computer processor tracks a shape of said device.

14. The system of claim 13, wherein said computer processor continuously tracks shape of said device with time.

15. The system of claim 1, wherein said optical fiber comprises one or more sets of 3 fluorophores with different emission spectra embedded in said cavities and spaced around the circumference of the fiber, wherein said fluorophores are positioned to report bendloss of light when said optical fiber is bent.

16. The system of claim 1, wherein said cavities each comprises a single type of fluorophore, and wherein said fibers comprises a plurality of fluorophores having different spectral properties.

17. A method for tracking a device, comprising:
a) positioning a device comprising an optical fiber, said optical fiber comprising a core and a cladding surrounding the core, wherein said cladding comprises a plurality of cavities such that light leakage from the core through the cladding occurs when a bend is present in the fiber; and wherein said cavities contain a fluorphore that generates a fluorescent emission in response to said light leakage into an environment, and wherein the intensity of said fluorescent emission is proportional to the degree of bend in said fiber;
b) directing light through the optical fiber such that when the optical fiber is bent, light lost through bendloss excites said fluorophore;
c) measuring fluorescent emission from said fluorphore with a detector that measures said fluorescent emission; and
d) tracking said device from said measured fluorescent emission with a computer processor that processes data associated with said fluorescent emission.

18. The method of claim 17, wherein said device is a guide wire.

19. The method of claim 17, wherein said device is an endoscope.

20. The method of claim 17, wherein said tracking comprises tracking of shape of said device.

21. The method of claim 20, wherein said tracking comprises continuous tracking of shape of said device with time.

22. The method of claim 17, wherein excitation of said one or more fluorophores results in emitted light at a longer wavelength back into the core and wherein said measuring comprises measuring said fluorescent emission at the end of the fiber.

* * * * *